United States Patent [19]
Arkans

[11] Patent Number: 6,007,559
[45] Date of Patent: Dec. 28, 1999

[54] VASCULAR ASSIST METHODS AND APPARATUS

[75] Inventor: Edward J. Arkans, Carlsbad, Calif.

[73] Assignee: ACI Medical, San Marcos, Calif.

[21] Appl. No.: 09/096,757

[22] Filed: Jun. 12, 1998

[51] Int. Cl.⁶ ................................................. A61B 17/00
[52] U.S. Cl. ......................................... 606/201; 606/202
[58] Field of Search .................................. 606/201, 202, 606/203, 104; 601/140–160

[56] References Cited

U.S. PATENT DOCUMENTS

| | | | |
|---|---|---|---|
| 4,013,069 | 3/1977 | Hasty | 601/152 |
| 4,029,087 | 6/1977 | Dye et al. | 128/24 |
| 4,030,488 | 6/1977 | Hasty | 128/24 |
| 4,066,084 | 1/1978 | Tillander | 601/152 |
| 4,320,746 | 3/1982 | Arkans et al. | 128/24 |
| 4,402,312 | 9/1983 | Villari et al. | 128/24 |
| 5,007,411 | 4/1991 | Dye | 128/64 |
| 5,117,812 | 6/1992 | McWhorter | 128/24 |
| 5,179,941 | 1/1993 | Siemssen et al. | 128/40 |
| 5,186,163 | 2/1993 | Dye | 128/64 |
| 5,218,954 | 6/1993 | Van Bemmelen | 128/24 |
| 5,383,894 | 1/1995 | Dye | 128/648 |

Primary Examiner—Michael Buiz
Assistant Examiner—Lien Ngo
Attorney, Agent, or Firm—Workman, Nydegger & Seeley

[57] ABSTRACT

A vascular assist device which maintains a static graduated pressure as the minimum pressure at all times during use. At least two inflatable chambers which wrap around selected portions of a limb apply elevated pressure to selected portions of a limb to disgorge blood therefrom. The inflatable chambers also apply static pressure which is graduated from distal to proximal along selected portions of a limb, such as from the ankle to the hip. A separate inflatable foot chamber can be included and is not necessarily utilized in conjunction with the compression phases for the ankle, calf, or thigh inflatable chambers. A desired pressure level is generated and maintained in a pressure accumulator, and a pressure regulator and regulator valve control the pressure in the inflatable chambers. The inflatable chambers between the ankle and hip are inflated to a predetermined and uniform dynamic pressure which is maintained in the inflatable chambers for a predetermined amount of time. The pressure is then decreased to a static pressure level which is graduated in pressure from the most distal inflatable chamber to the most proximal inflatable chamber between the ankle and the hip. The cycle is repeated after maintaining graduated static pressure for about forty five seconds.

35 Claims, 3 Drawing Sheets

VASCULAR ASSIST METHODS AND APPARATUS

BACKGROUND OF THE INVENTION

1. The Field of the Invention

The present invention relates generally to apparatus and methods for improving vascular blood flow, and more particularly to apparatus and methods for improving venous blood flow from peripheral vessels.

2. The Relevant Technology

Blood clotting is a body's natural response at the site of a cut to help seal damaged blood vessels and minimize blood loss. However, a blood clot can also form in an intact vessel, in an inflamed vessel, or in a vessel that contains fatty deposits. Clots tend to form when blood flow is sluggish or in circumstances where there is a rise in the level of coagulation factors in the blood. Deep vein thrombosis, for example, is a condition wherein such clotting occurs within deep-lying veins, especially of the leg. Deep vein thrombosis is common in people with heart failure and in those who have suffered strokes or who are immobilized for long periods of time. In addition, deep vein thrombosis commonly occurs after knee, hip, or abdomen surgery. Age and obesity are also contributory factors. Symptoms of deep vein thrombosis include pain, tenderness, swelling, discoloration, and ulceration of the skin.

Once a clot has formed, it may provide a site for further clotting along the length of the vein. These clots, known as thrombi, can cause pain and damage to the tissues served by the vessel. A clot, or thrombus, that breaks away from the vessel into the blood stream is called an embolus. A "pulmonary embolism" can occur when an embolus travels from peripheral veins through the heart to the lungs via a pulmonary artery. In the lungs, the emboli can be trapped in the ever-decreasing branches of the bronchi. If the embolus is large enough to block the pulmonary artery, or if there are many emboli, the condition can be life threatening. Physicians have long sought effective procedures capable of averting this condition.

One approach used by physicians has involved the administration of anticoagulant drugs such as heparin. Anticoagulant drugs are given in an effort to reduce the clotting ability of the blood and the chance of more clots occurring. However, anticoagulants may be contraindicated in many patients. For example, these drugs may detrimentally result in abnormal bleeding in different parts of the body of the patient and may hinder necessary clotting at a surgical site.

Physicians have also recommended that a patient become ambulatory, or walk around, as soon as possible after surgery. However, it should be appreciated that this is not always feasible for many post-operative patients. In fact, patients who have undergone serious surgical procedures may not be ambulatory for an indeterminate period of time after the surgery.

Physicians have also utilized special elastic stockings, which apply rather tight pressure at the foot and gradually decreasing pressure up to the thigh or pelvis, in an attempt to avert deep vein thrombosis. These stockings are typically opaque and limit the ability of health care personnel to visualize the limb beneath the stocking, except for small fenestrations at the toe area. Thus, in order to monitor the condition of the limb, the stockings must be removed repeatedly throughout use.

In theory, elastic stockings allow a high degree of mobility for the patient. However, in practice, maintaining the stockings at the thigh or pelvis level during ambulation has presented a problem, and garters are often necessitated to hold the stockings in place. It should be appreciated that male patients are generally displeased, if not completely uncooperative, about wearing stockings with garters.

Yet, stockings that roll down present further problems for the patient. Because the stockings increase in pressure as they approach the foot, a tourniquet effect is created when the stockings roll down. Essentially, increased pressures result when the stockings roll down due to doubling or tripling of compressive layers, which generally has the effect of doubling or tripling the applied pressure. Blood flow actually becomes blocked, which may result in ischemic damage to distal tissues and further clotting of the stagnant blood. Thus, elastic stockings actually necessitate close monitoring by health care personnel in order to prevent the tourniquet effect. Surprisingly, elastic stockings are often given to home care patients where little, if any, monitoring is available.

In addition, elastic stockings are not "one size fits all." An imprecise fit can lead to too much pressure and the tourniquet effect if the stockings are too small, and to a substantially diminished effect if the stockings are too large. Therefore, the effectiveness of the elastic stockings typically depends upon a fitting prior to use. Yet, this may be burdensome for the patient, and requires the physician to determine at-risk patients in advance. It should be appreciated that not all procedures associated with the risk for deep vein thrombosis are planned ahead of time. In addition, the fitting requirement necessitates a large inventory of elastic stockings, which may be an inefficient use of capital and stock space.

Another method employed by physicians utilizes pneumatic compression devices. Such devices are generally attached to the patient's calf area while approximately 50 mmHg of pressure is applied for 10–15 seconds and then reduced to atmospheric pressure for 45 to 60 seconds. These devices are also utilized with compression occurring slowly up the calf and thigh in sequential pressure cycles. Pneumatic devices are generally utilized in higher risk patients with reduced mobility because the device itself limits ambulation.

Physicians have also combined the use of elastic stockings and pneumatic devices. However, such a combination presents the problems inherent in the two methods as well as added defects. The cost is virtually doubled, as is the amount of attention required by the medical personnel. Additionally, the devices in concert are hot and uncomfortable. Furthermore, the stocking may roll down beneath the pneumatic device and, as described above, result in a tourniquet effect which increases stagnation and potential clotting of the blood, the very symptoms the devices intended to prevent.

SUMMARY AND OBJECTS OF THE INVENTION

It is therefore an object of the present invention to provide apparatus and methods for prophylaxis against deep vein thrombosis.

Yet another object of the present invention is to provide methods and apparatus for prophylaxis against deep vein thrombosis that promote patient compliance and comfort.

Another object of the present invention is to provide methods and apparatus for prophylaxis against deep vein thrombosis that allow health care personnel to visualize the patient's limb, and especially the skin, beneath the apparatus.

Still another object of the present invention is to provide methods and apparatus for prophylaxis against deep vein thrombosis that decrease the hassle and burden typically associated with fitting of certain prior art devices.

It is yet another object of the present invention to provide methods and apparatus for prophylaxis against deep vein thrombosis in a supine patient.

It is still another object of the present invention to provide apparatus and methods for prophylaxis against deep vein thrombosis that prevents further blood stagnation as a result of the tourniquet effect.

These and other objects and features of the present invention will become more fully apparent from the following description and appended claims, or may be learned by the practice of the invention as set forth hereinafter.

To achieve the forgoing objects, and in accordance with the invention as embodied and broadly described herein, the present invention relates to a vascular assist device which maintains a static graduated pressure as the minimum pressure at all times during use. The present invention incorporates at least one compression sleeve which wraps around portions of a limb. The compression sleeve includes inflatable chambers which apply elevated pressure to selected portions of a limb to disgorge blood therefrom. The inflatable chambers also apply static pressure which is graduated from distal to proximal along selected portions of a limb.

In order to use the apparatus of the present invention, a compression sleeve is attached around at least one limb of a patient. A desired pressure level is then generated and maintained in a pressure accumulator. A pressure regulator and regulator valve control the pressure in the inflatable chambers of the compression sleeve. The inflatable chambers associated with the compression sleeve from the ankle to the hip are inflated to a predetermined and uniform dynamic pressure. This pressure is maintained in the inflatable chambers for a predetermined number of seconds. The pressure is then decreased to a static pressure level which is graduated in pressure from the ankle to the hip from a distal inflatable chamber to the most proximal inflatable chamber. The cycle is repeated after maintaining graduated static pressure for about forty five seconds.

BRIEF DESCRIPTION OF THE DRAWINGS

In order to more fully understand the manner in which the above-recited and other advantages and objects of the invention are obtained, a more particular description of the invention will be rendered by reference to a specific embodiment thereof which is illustrated in the appended drawings. Understanding that these drawings depict only a typical embodiment of the invention and are not therefore to be considered to be limiting of its scope, the invention in its presently understood best mode for making and using the same will be described and explained with additional specificity and detail through the use of the accompanying drawings in which.

DETAILED DESCRIPTION OF THE PREFERRED EMBODIMENTS

Deep vein thrombosis is a condition wherein clotting occurs within deep-lying veins, most commonly in the leg. These clots may break away from the vessel and enter into the blood stream and thereafter cause serious problems. For example, in a condition known as a pulmonary embolism, a blood clot, or embolus, travels from a peripheral vein to the lungs via one of the pulmonary arteries. If the embolus is large enough to block the pulmonary artery, or if there are many emboli, the condition can be life threatening. Physicians have therefore struggled with various approaches in the hopes of averting this condition.

The present invention, which is directed to new and improved methods and apparatus for providing prophylaxis against deep vein thrombosis, is a significant advance in the art. It has been discovered that the problems of prior approaches can be lessened or avoided by utilizing dynamic compression cycles with decompression cycles that maintain minimum graduated static compression levels. The resulting advantages of the present invention include, but are not limited to, improved clinical efficacy, lower cost, less hospital inventory, less inconvenience for the patient, and less risk for a tourniquet effect.

Figure 1:
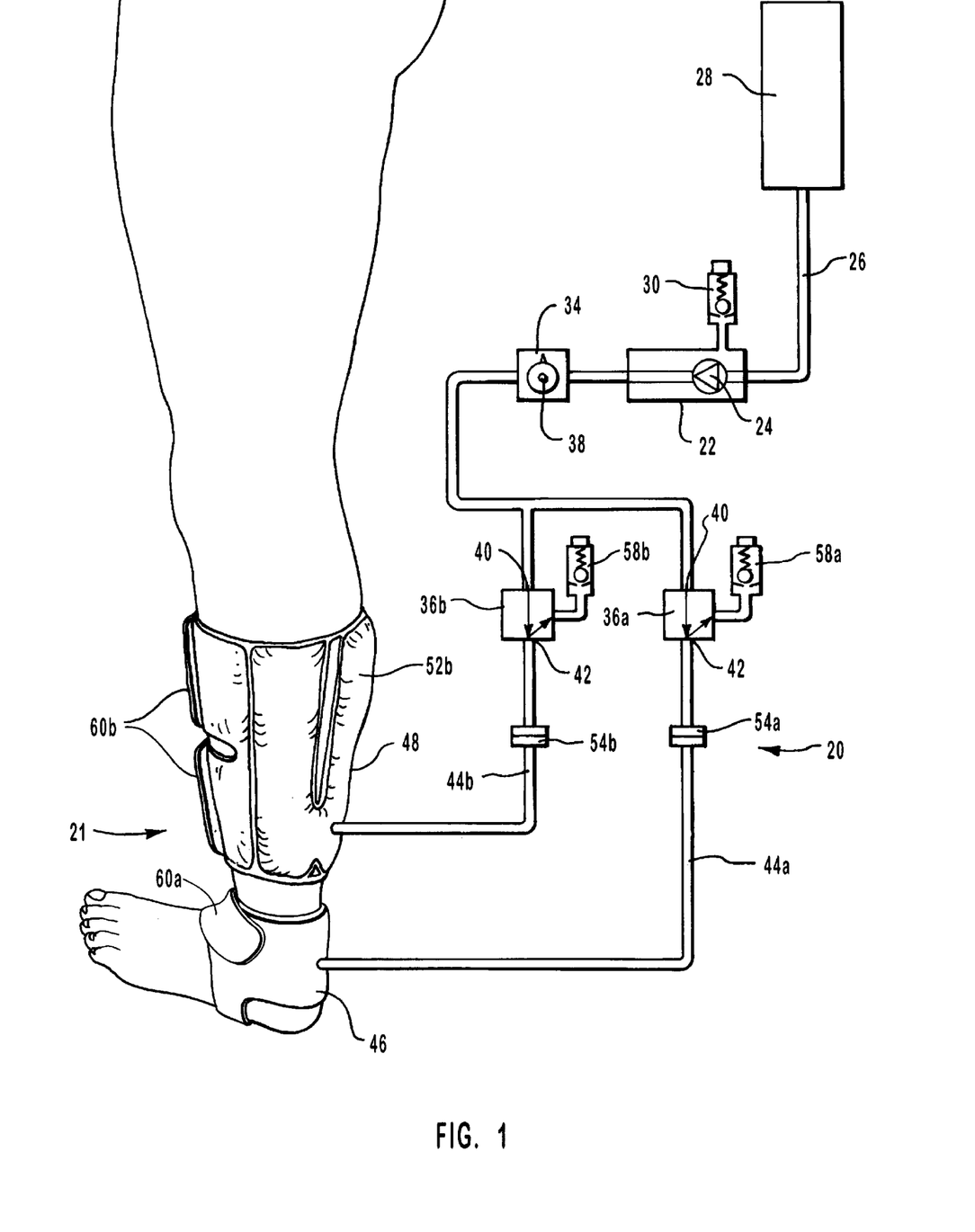
FIG. 1 is a diagrammatic view of the system of the present invention.
Figure 2:
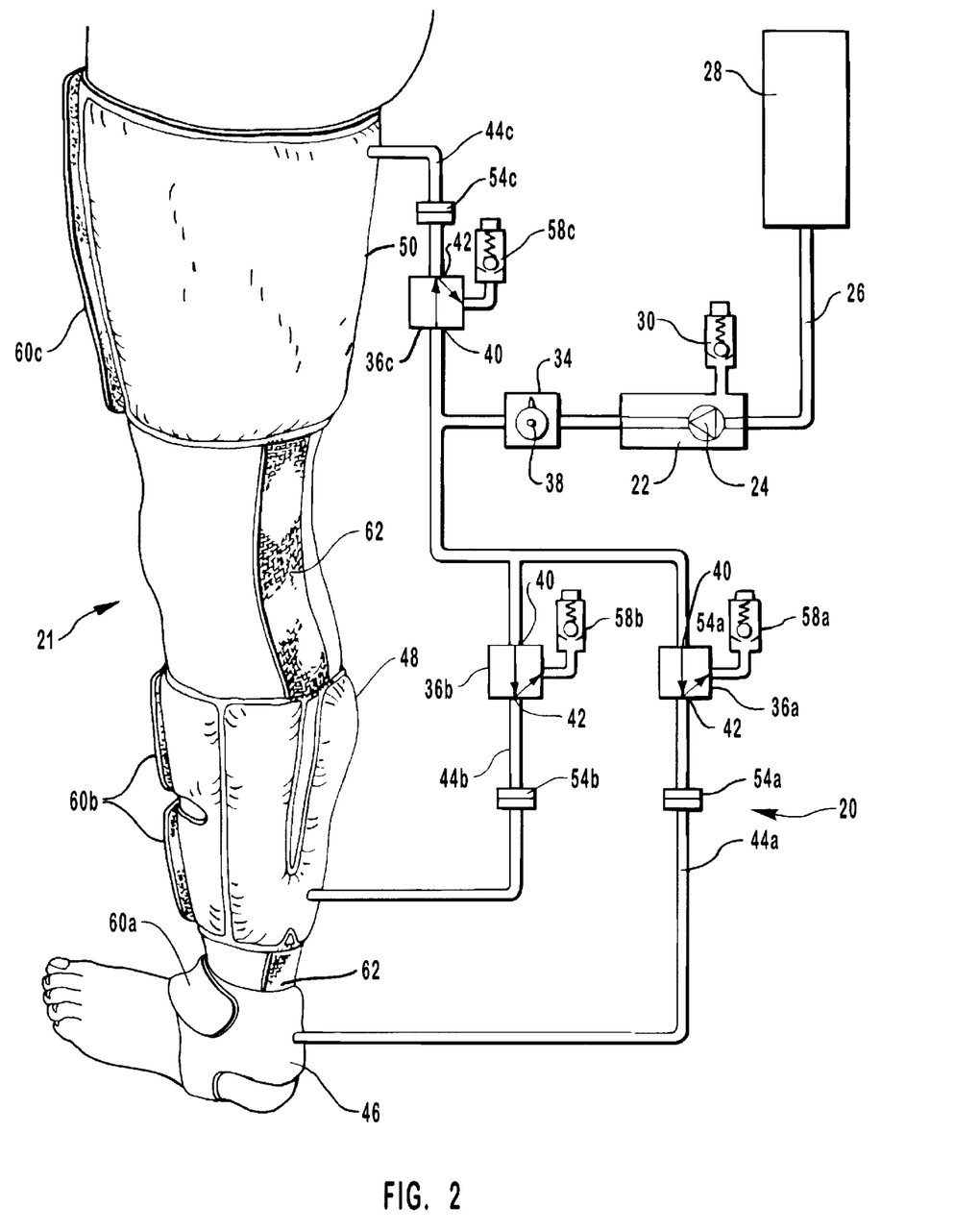
FIG. 2 is a diagrammatic view of an alternate embodiment of the system of the present invention.
Figure 3:
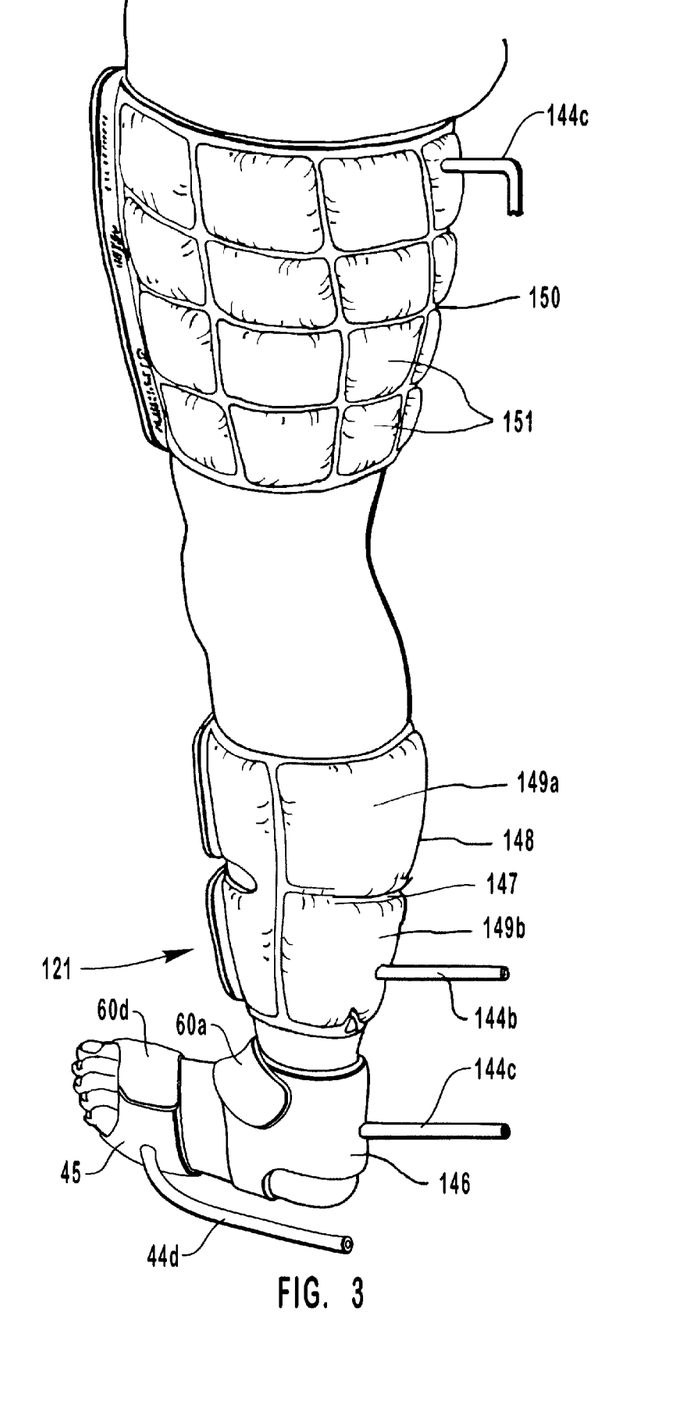
FIG. 3 is a diagrammatic view of another alternate embodiment of the system of the present invention.

Referring to the drawings, FIG. 1 depicts one presently preferred embodiment of an apparatus, generally labelled 20, for providing prophylaxis against deep vein thrombosis. The apparatus preferably comprises a compression sleeve, generally labelled 21. A compression sleeve in accordance with the present invention comprises inflatable chambers, which will be described in more detail hereinbelow, and which are spaced apart or side by side on a limb of a patient. In FIG. 1, for example, compression sleeve 21 extends from the ankle to the calf portion of a patient's leg. In FIG. 2, compression sleeve 21 extends from the ankle to the thigh portion of a patient's leg. In FIG. 3, compression sleeve 21 extends from the foot to the thigh portion of a patient's leg. Additional features and components of the compression sleeves will be described in more detail hereinbelow.

Apparatus 20 preferably comprises an accumulator 22 which serves as a means for maintaining pressure during use of the apparatus. It should be appreciated that other means for maintaining pressure would also be within the scope of the present invention. For example, the means for maintaining pressure may comprise an air tank. Alternatively, any other energy storage elements such as a spring-loaded diaphragm, or a spring-loaded piston and cylinder would serve as means for maintaining pressure within the scope of the present invention.

It is a feature of the present invention that accumulator 22 maintains a consistently elevated pressure during use. In addition, accumulator 22 preferably maintains a pressure level above the pressure levels for the remaining portions of the apparatus to be described more fully herein. Accumulator 22 preferably maintains a pressure level at a range from about 6 to about 35 psi during use. More preferably, accumulator 22 maintains a pressure level at a range from about 15 to about 25 psi. Most preferably, accumulator 22 maintains a pressure level at about 20 psi.

Accumulator 22 preferably includes accumulator valve 30 which facilitates maintenance of a desired accumulator pressure level such as described above. In a preferred embodiment illustrated in FIG. 1, accumulator valve 30 comprises a spring loaded check valve. Alternatively, accumulator valve may comprise a weight loaded check valve. In addition, it should be appreciated that other means for maintaining a desired pressure level within accumulator would be within the scope of the present invention. For example, a pressure switch, which is set to a particular pressure measurement and turns on and off accordingly, is within the scope of the present invention.

In order to generate pressure, accumulator preferably includes pump 24 designed for drawing fluid into accumulator. Pump 24 preferably resides inside accumulator 22, as illustrated in FIG. 1. Alternatively, the pump may reside on the outside of accumulator, as in the case of an external pump.

The pump may comprise a cylinder with a piston moved with a linear drive mechanism that compresses the fluid from the fluid source. The linear drive mechanism may include a motor and associated mechanism which converts the motor's rotational motion to linear motion. The linear drive mechanism may alternatively include a vibrating piston moved back and forth by a changing magnetic field applied to the piston.

Alternatively, the pump may comprise a form of bellows with an actuator and rigid sides that collapse the bellows and compress the fluid therein. It will be appreciated from the teachings contained herein that any other suitable pressure generator would be within the scope of the present invention.

In a preferred embodiment illustrated in FIG. 1, pump 24 comprises inlet 26 in fluid communication with fluid source 28. The fluid source preferably comprises any compressible fluid such as oxygen or nitrogen, both of which may reside in an external gas tank or are centrally available in most hospitals. The fluid source may alternatively comprise air from the atmosphere of the room in which the apparatus of the present invention resides. Alternatively, the fluid source may comprise a non-compressible fluid, such as water or other liquid, working in concert with a compressible fluid. It should be appreciated that the fluid source may alternatively comprise compressed gases supplied by the hospital, in which case use of the pump may not be necessary.

Accumulator 22 pressurizes the fluid from fluid source 28, whereupon pressurized fluid preferably travels into pressure regulator 34. The pressure regulator preferably maintains a pressure level from about 20 mmHg to about 150 mmHg. The pressure regulator may comprise a pressure switch or transducer to monitor pressure and communicate with regulator valves to allow fluid flow to the inflatable chambers, as will be described in more detail hereinbelow.

Further, pressure regulator serves as a means for regulating pressure in each inflatable chamber independent of each other inflatable chamber, as will be described in more detail hereinbelow. It should be appreciated that other means for regulating pressure in each inflatable chamber would be within the scope of the present invention. By way of example only, a fluid activated solenoid valve, disks that rotate with respect to one another such that the disks' holes align in time to provide pressurized fluid flow paths, or an electrical coil with linear or rotational translation, could serve as means for regulating pressure in each inflatable chamber.

In a preferred embodiment of the present invention illustrated in FIG. 1, pressure regulator 34 is in fluid communication with regulator valves, 36a and 36b. The embodiment of the present invention illustrated in FIG. 2, wherein like features are represented by like numerals, adds regulator valve 36c. Each regulator valve preferably comprises an electrically activated three-way solenoid.

By way of example only, and not limitation, the electrically activated solenoid contains an electromagnet, such as a coil of wire that generates a magnetic field when current passes through it. This magnetic field causes an armature to move in the linear axis of the coil. This armature creates a seal to an internal fluid passage and allows fluid to flow through the passage depending on the presence or absence of current, and driven by an external timing mechanism. The electrically activated solenoid of the present invention, is driven by timer circuit 38 housed in pressure regulator 34 as illustrated in FIG. 1. Alternatively, the timer circuit may be situated on a printed circuit board external to a pressure regulator.

In a preferred embodiment illustrated in FIG. 1, each regulator valve includes a pressure inlet 40, an exhaust valve 58, and a pressure outlet 42. Pressure inlet 40 is in direct fluid communication with pressure regulator 34, such that pressurized fluid 32 enters regulator valve through pressure inlet 40. Pressure outlet 42 is in fluid communication with connective member 44a, 44b such that upon proper solenoid alignment, pressurized fluid travels through pressure outlet 42 and into connective member 44a, 44b.

Each connective member connects to an inflatable chamber, which applies compressive forces to designated areas of a limb. Further each connective member serves as a means for introducing fluid into an inflatable chamber preferably independent of each other inflatable chamber. It should be appreciated that other means for introducing fluid into an inflatable chamber would be within the scope of the present invention. For example, any fluid conduit could serve as means for introducing fluid. Alternatively, each inflatable chamber could include a regulator valve directly attached thereto.

In addition, it should be appreciated that it is preferable to permit removable connections between the inflatable chambers and the regulator valves such that positioning of the compression sleeve on a patient is facilitated. Therefore, each connective member is preferably removably attached to each corresponding inflatable chamber. In the embodiment of the present invention depicted in FIG. 1, each inflatable chamber is in fluid communication with a connector 54a, 54b, which facilitates removable attachment of each inflatable chamber to each connective member. FIG. 2 adds connector 54c for removable attachment of thigh inflatable chamber 50 to connective member 44c. FIG. 3 adds a separate connector (not shown) for removable attachment of foot inflatable chamber 45 to connective member 44d.

It should also be appreciated that a plurality of inflatable chambers is within the scope of the present invention. Deep vein thrombosis occurs in the deep lying veins of the leg, such as the anterior and posterior tibial (calf), the femoral (thigh), and the iliac (pelvis/hip) veins. Therefore, the present invention incorporates inflatable chambers in at least one, and preferably more than one, of these key areas. In the embodiments of the present invention illustrated in FIGS. 1, 2 and 3, a different inflatable chamber is associated with each regulator valve and each corresponding connective member.

For example, in FIG. 1, ankle inflatable chamber 46, which is designed to apply compressive forces to designated areas of the ankle, is removably connected to regulator valve 36a via connective member 44a. Similarly, calf inflatable chamber 48, which is designed to apply compressive forces to designated areas of the lower leg and particularly the calf, is removably connected to regulator valve 36b via connective member 44b. In FIG. 2, thigh inflatable chamber 50, which is designed to apply compressive forces to designated areas of the upper leg and particularly the thigh, is removably connected to regulator valve 36c via connective member 44c. In FIG. 3, foot inflatable chamber 45, which is designed to apply compressive forces to designated areas of the foot, is removably connected to a separate regulator valve (not shown) via connective member 44d.

Although only a single limb is depicted in the figures, it should be appreciated that the present invention is directed to an apparatus for prophylaxis against deep vein thrombosis for one or more limbs. In turn, each regulator valve is preferably connected to inflatable chambers on more than one limb. Thus, regulator valve 36a is preferably connected to two ankle inflatable chambers, regulator valve 36b is preferably connected to two calf inflatable chambers, and regulator valve 36c is preferably connected to two thigh inflatable chambers, such that each leg receives simultaneous treatment, for example.

Each inflatable chamber preferably includes a retaining means for retaining the inflatable chamber substantially against selected portions of a limb. In a preferred embodiment of the present invention illustrated in FIG. 1, such retaining means comprises retaining straps 60a, 60b. Ankle inflatable chamber 46 incorporates retaining strap 60a which substantially retains ankle inflatable chamber at the ankle of a patient. Calf inflatable chamber 48 incorporates retaining straps 60b which substantially retain calf inflatable chamber at the calf of a patient. In addition, FIG. 2 illustrates thigh inflatable chamber 50 which incorporates retaining strap 60c for substantially retaining thigh inflatable chamber at the thigh of the patient. FIG. 3 illustrates foot inflatable chamber 45 which incorporates retaining strap 60d for substantially retaining foot inflatable chamber around the foot of the patient.

Each retaining strap preferably optimizes patient fit and comfort while the patient is wearing the compression sleeve of the present invention. Further, each retaining strap preferably comprises hook and pile material such as that used in fasteners like Velcro®. Alternatively, each retaining strap may incorporate buttons, snaps, or other fastening device which will retain compression sleeve substantially against an appropriate portion of a limb. It should be appreciated that other retaining means for retaining the compressive chamber substantially against portions of a limb would be within the scope of the present invention.

Each inflatable chamber further serves as a compressive means for applying a compressive force to selected portions of a limb. In a preferred embodiment of the present invention illustrated in FIG. 1, ankle inflatable chamber 46 applies compressive force to a patient's ankle. Calf inflatable chamber 48 applies compressive force to a patient's calf. In addition, FIG. 2 illustrates thigh inflatable chamber 50 for applying compressive force to a patient's thigh. FIG. 3 illustrates foot inflatable chamber 45 for applying compressive force to a patient's foot. It will also be appreciated that an additional inflatable chamber may be provided in accordance with the present invention for applying compressive force to a patient's pelvis and hip area.

Preferably, each inflatable chamber is targeted to a particular area of the limb and as such is sized accordingly. For example, as illustrated in FIG. 2, the ankle inflatable chamber is smaller than the thigh inflatable chamber. However, it should be understood that a uniform size for the inflatable chambers would also be within the scope of the present invention.

It should also be appreciated that each inflatable chamber may comprise one continuous chamber, or may be subdivided into a plurality of individual, smaller inflation sub-chambers within. For example, FIG. 3 illustrates an embodiment of the present invention wherein calf inflatable chamber 148 is subdivided into two inflation sub-chambers 149a, 149b. Calf inflation chamber 148 as a whole is inflated independently from ankle inflatable chamber 146. The sub-inflation chambers 149a, 149b within the calf inflation chamber are in fluid communication with one another, and are addressed by a single connective member 144b.

FIG. 3 further illustrates an alternate embodiment of thigh inflatable chamber 150 comprising a plurality of inflation sub-chambers 151, wherein all inflation sub-chambers are addressed by a single connective member 144c.

It should also be appreciated that flow restricted communication between the sub-chambers may also be incorporated to further enhance the therapeutic features of the present invention. For example, in the embodiment depicted in FIG. 3, the more distal inflation sub-chamber 149b will inflate slightly prior to the more proximal inflation sub-chamber 149a due to flow restriction member 147 between the two sub-chambers. This approximates a peristaltic disgorgement of the blood from the vessels.

By tailoring the locations and extent of the inflatable chamber or chambers within the compression sleeve, each inflatable chamber may be held against desired portions of the limb in order to apply compressive forces thereto. In a preferred embodiment of the present invention, each inflatable chamber is preferably situated partially circumferential to the limb. That is, the inflatable chamber does not completely encircle the outer diameter of the limb. For example, one inflatable chamber is held against the dorsal side of the calf as illustrated in FIG. 1. However, the inflatable chamber could alternatively completely encircle the limb.

Each inflatable chamber is in fluid communication with a corresponding connective member, such that connective members 44a, 44b, and 44c correspond to ankle inflatable chamber 46, calf inflatable chamber 48, and thigh inflatable chamber 50, respectively, as illustrated in FIG. 2. FIG. 3 adds separate connective member 44d for foot inflatable chamber 45. Upon inflation of an inflatable chamber by pressurized fluid flowing through a connective member, each inflatable chamber expands and exerts a compressive force on a particular portion of a limb corresponding to the particular inflatable chamber retained thereon.

It is believed that the problems associated with deep vein thrombosis are minimal in the veins of the foot. Thus, in preferred embodiments of the present invention such as those illustrated in FIGS. 1 and 2, the compression sleeve 21 originates distally at the ankle. However, in an alternate embodiment of the present invention depicted in FIG. 3 and to be described in more detail hereinbelow, the compression sleeve 121 includes a foot inflatable chamber which supplements the compression provided by the inflatable chambers located between the ankle and the hip of the patient.

During the dynamic compression phase, all inflatable chambers from the ankle to the hip preferably approach a substantially equal pressure level. In a preferred embodiment of the present invention, the pressure level approaches about 50 mmHg to about 150 mmHg. Alternatively, the resulting pressure level may be graduated from the ankle to the hip, (distal to proximal). The dynamic compression phase of the present invention facilitates emptying of the vessels and thus effectuates the movement of blood from the distal portions of a limb. The dynamic compression for the foot inflatable chamber preferably approaches a pressure level from about 10 mmHg to about 150 mmHg.

During the static compression phase, each inflatable chamber is deflated to a pressure level less than the pressure level that it experienced during the dynamic compression phase. Each inflatable chamber preferably deflates to an extent, but still exerts a low pressure level of compressive force on each selected portion of a limb. It is therefore a feature of the present invention that a static pressure level is maintained at all times during use of the compression sleeves. This static pressure level is preferably graduated distal to proximal, from the ankle to the hip. The static pressure level of the foot inflatable chamber is preferably excluded from this pressure gradient. By way of example only, and not limitation, the ankle inflatable chamber maintains a higher static pressure than the calf inflatable chamber, and the calf inflatable chamber maintains a higher static pressure than the thigh inflatable chamber. The static compression phase therefore effectuates movement of blood back into the distal portions of a limb and thus facilitates refilling of the vessels.

An exhaust valve 58a, 58b in FIG. 1, and in FIG. 2, 58c, is attached to each of the regulator valves 36a, 36b, and 36c, respectively. In a preferred embodiment of the present invention, exhaust valve comprises a spring loaded ball against an inlet orifice. The spring compression and ball diameter are preferably adjustable to accommodate the pressure gradient described hereinbelow. It should be appreciated, however, that other exhaust valves, such as weight loaded check valves, or spring loaded disks, would be within the scope of the present invention.

Each exhaust valve preferably facilitates the static compression phase and resultant pressure gradient in the inflatable chambers. During each static compression phase, pressurized fluid exits each inflatable chamber and returns to the corresponding regulator valve where it leaves through the exhaust valve. It is a feature of the present invention that each exhaust valve is directed to a predetermined pressure level for the appropriate area of the limb and corresponding inflatable chamber, which allows graduated static pressure during each static compression phase.

In particular, exhaust valve 58a associated with ankle inflatable chamber, preferably permits deflation to a static compression level from about 15 to about 25 mmHg. More preferably, exhaust valve 58a permits deflation of ankle inflatable chamber to a static compression level from about 16 to about 20 mmHg. Most preferably, exhaust valve 58a permits deflation of ankle inflatable chamber to a static compression level of about 18 mmHg.

Furthermore, during each static compression phase, exhaust valve 58b associated with calf inflatable chamber preferably permits deflation to a static compression level from about 10 to about 20 mmHg. More preferably, exhaust valve 58b permits deflation of calf inflatable chamber to a static compression level from about 13 to about 17 mmHg. Most preferably, exhaust valve 58b permits deflation of calf inflatable chamber to a static compression level of about 14 mmHg.

During each static compression phase when thigh inflatable chamber is utilized, exhaust valve 58c preferably permits deflation of thigh inflatable chamber to a static compression level from about 5 to about 15 mmHg. More preferably, exhaust valve 58c permits deflation of thigh inflatable chamber to a static compression level from about 6 to about 14 mmHg. Most preferably, exhaust valve 58c permits deflation of thigh inflatable chamber to a static compression level of about 8 mmHg.

A separate exhaust valve (not shown) is also attached to the regulator valve associated with the foot inflatable chamber 45. During static compression when the foot inflatable chamber is utilized, the exhaust valve permits deflation of the foot inflatable chamber to a static compression level from about 5 to about 30 mmHg. In a preferred embodiment of the present invention, the foot inflatable chamber is not included in the pressure gradient established during static compression. Thus, the pressure level of the foot inflatable chamber is preferably less than the pressure level in the next more proximal inflatable chamber. Alternatively, the static compression pressure level of the foot inflatable chamber is equal to or greater than the pressure level in the next more proximal inflatable chamber.

It should be appreciated that each exhaust valve is adjustable. Furthermore, additional exhaust valves would be associated with inflatable chambers utilized with additional limb segments, with static pressure values for each static compression phase decreasing as the inflatable chambers proximally approach the heart.

All inflatable chambers may be attached to form a continuous compression sleeve 21 as illustrated in FIG. 2 wherein attachment portion 62 is depicted behind the knee portion of a patient's limb. Attachment portion 62 may be a strip of material such as the pile material utilized with the retaining strap. Although not required, it is preferred that attachment portion not contain an inflatable chamber. It is preferable that the inflatable chambers be separated within the compression sleeves to ensure graduated static pressure. Further, the use of separate inflatable chambers allows separate compressive forces to be exerted where desired. Alternatively, in the embodiments illustrated in FIGS. 1 and 3, the inflatable chambers are unconnected by any attachment portion, thus compression sleeves 21, 121 are discontinuous.

It is a feature of the present invention that a pressure switch may be incorporated as a safety device, such as within the pressure regulator. The pressure switch preferably causes an alarm to sound, or shuts down the device if pressure exceeds dangerously high levels or if pressures are elevated for extended amounts of time. For example, a pressure switch may be incorporated on the accumulator to turn the pump off in the event that the accumulator pressure becomes excessively high. It should be understood that the pressure switch may also be utilized for turning the pump on when the pressure falls too low.

It is an additional feature of the present invention that the apparatus maintains visual openings during use of the apparatus on the limb of a patient, such that open regions allow observations of the skin and underlying structures. In turn this permits health care personnel to asses the health of the skin tissue of the limb by directly observing skin color and texture.

The present invention is additionally directed to methods for use of the vascular assist device. The health care professional determines the areas of the limb or limbs that would benefit from the present invention. The health care professional can position the appropriate inflatable chambers before, during, or after surgery as per the preference of the physician, or the needs of the patient. The inflatable chambers of the present invention are preferably disconnected from the regulator valves such that positioning of each sleeve on the patient is facilitated.

In the preferred method of the present invention, the accumulator is primed and pressurized. The regulator then supplies pressurized fluid to each inflatable chamber through each corresponding regulator valve. All inflatable chambers along the limb from the ankle to the hip are preferably inflated to a predetermined and uniform dynamic pressure, such as from about 50 mmHg to 150 mmHg. All inflatable chambers from the ankle to the hip are preferably deflated to a predetermined and graduated static pressure, such that the most distal pressure along the limb from the ankle to the hip is slightly higher than the next most distal pressure.

Neither inflation nor deflation is necessarily simultaneous. In fact, the inflation, deflation, and delay rate, as well as the pressure for the inflatable chambers are adjustable. For example, when inflating both the ankle and calf inflatable chambers, an inflation delay time between the start of inflation for each portion can be used and adjusted from zero seconds (for simultaneous inflation) to about two or more seconds (for progressive inflation). In one embodiment, the inflatable chambers are rapidly inflated and held at the preselected inflation pressure for between 3 seconds to 15 seconds, although longer or shorter times would be within the scope of the present invention. When progressive inflation is used, the ankle inflatable chamber is inflated first with the calf portion being inflated at some time later. When used together, the inflation time, deflation time, and pressure for both the ankle portion and the calf portion (and thigh and/or hip portion if used) may be the same, or they may be different to tailor the treatment regime to the individual patient.

The preferred inflation cycle for each dynamic compression phase is about 3 seconds at 45 mmHg to 150 mmHg in the ankle inflatable chamber. Then after a delay for about 0.5 to 4 seconds, the next more proximal inflatable chamber is inflated and so on.

The preferred deflation cycle for each static compression phase occurs in the same order as inflation. Deflation is from about 17–60 seconds, and most preferably 45–60 seconds, which provides a better filling of the veins.

Alternatively, the dynamic compression phase may terminate with simultaneous deflation to static compression phase levels.

In an alternate method of the present invention, foot inflatable chamber 45 is utilized in conjunction with the ankle, calf, and/or thigh inflatable chambers. Because deep vein thrombosis is believed to be minimal in the veins of the foot, the foot inflatable chamber does not necessitate the dynamic compression and the graduated static compression features of the ankle, calf, and/or thigh inflatable chambers as described hereinabove. In one embodiment, the foot inflatable chamber is inflated to a dynamic compression level and deflated to a static compression level simultaneously with the ankle inflatable chamber. Alternatively, the foot inflatable chamber is inflated and deflated prior to the ankle inflatable chamber in a progressive manner such as described above. Preferably the inflation and deflation cycles for the foot inflatable chamber are similar to the cycles described hereinabove with respect to the ankle, calf and/or thigh inflatable chamber. That is, the foot inflatable chamber preferably has a dynamic compression phase of about 3 seconds followed by a static compression phase of about 17 to about 60 seconds.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An apparatus for providing prophylaxis against deep vein thrombosis, comprising:
   (a) a plurality of inflatable chambers adapted for placement on a limb of a patient at risk for deep vein thrombosis such that at least two of said inflatable chambers are separated from each other to allow observation of the limb exposed therebetween,
   each of said inflatable chambers being adapted to apply a compressive force to the portion of the limb upon which each said inflatable chamber is placed;
   (b) means for introducing a fluid into each of said plurality of inflatable chambers; and
   (c) means for regulating pressure in a dynamic compression phase and a static compression phase within each of said inflatable chambers such that the dynamic compression phase and the static compression phase are independently controlled in each inflatable chamber,
   the dynamic compression phase establishing and maintaining a pressure in each of said plurality of inflatable chambers sufficient to effect movement of blood from the portion of the limb upon which each inflatable chamber is placed; and
   the static compression phase establishing a pressure gradient across the plurality of said inflatable chambers such that a higher static pressure is maintained at a distal inflatable chamber and a lower static pressure is maintained at a more proximal inflatable chamber, the static compression phase effecting a minimum pressure on the limb of the patient throughout attachment of the apparatus to the limb
   wherein each of the plurality of inflatable chambers is maintained during the static compression phase at static pressures sufficiently reduced below the dynamic compression phase in order to effect movement of blood back into the portion of the limb from which blood was removed during the dynamic compression phase.

2. An apparatus as recited in claim 1, wherein said inflatable chambers further comprise retaining means for retaining said inflatable chambers substantially against selected portions of the limb.

3. An apparatus as recited in claim 2, wherein said retaining means further comprise retaining straps including hook and pile material.

4. An apparatus as recited in claim 1, further comprising a regulator valve including an exhaust valve directed to a predetermined pressure level for an area of a limb and a corresponding inflatable chamber, said exhaust valve further facilitating graduated static pressure in said plurality of inflatable chambers.

5. An apparatus as recited in claim 4, wherein said exhaust valve comprises a spring loaded ball against an inlet orifice.

6. An apparatus as recited in claim 4, wherein said exhaust valve comprises a spring loaded disk against an inlet orifice.

7. An apparatus as recited in claim 1, wherein said means for introducing a fluid comprises a connective member.

8. An apparatus as recited in claim 7, wherein said connective member is removably attached to each inflatable chamber.

9. An apparatus as recited in claim 1, further comprising a foot inflatable chamber.

10. An apparatus for providing prophylaxis against deep vein thrombosis, comprising:
    (a) a first inflatable chamber, a second inflatable chamber, and a third inflatable chamber, said inflatable chambers being adapted to partially encircle and be releasably coupled to various portions of the leg of a patient,
    each of said inflatable chambers being adapted to apply a compressive force to the portion of the leg upon which each said inflatable chamber is placed;
    (b) a first attachment portion coupled between said first and second inflatable chambers and a second attachment portion coupled between said second and third inflatable chambers, the attachment portions maintaining separation between said inflatable chambers to allow observation of the leg of the patient;

(c) means for introducing a fluid into each of said inflatable chambers; and (d) means for regulating pressure in a dynamic compression phase and a static compression phase within each of said inflatable chambers such that the dynamic compression phase and the static compression phase are independently controlled in each inflatable chamber, the dynamic compression phase establishing a pressure in each of said inflatable chambers in order to effect movement of blood from the portion of the leg upon which each inflatable chamber is placed; and the static compression phase establishing a pressure gradient across said inflatable chambers such that a higher static pressure is maintained at a distal inflatable chamber and a lower static pressure is maintained at a more proximal inflatable chamber, the static compression phase effecting a minimum pressure on the leg of the patient throughout attachment of the apparatus to the leg.

11. An apparatus as recited in claim 10, wherein said inflatable chambers further comprise retaining means for retaining said inflatable chambers substantially against selected portions of the leg.

12. An apparatus as recited in claim 11, wherein said retaining means further comprise retaining straps including hook and pile material.

13. An apparatus as recited in claim 10, further comprising a regulator valve including an exhaust valve directed to a predetermined pressure level for an area of the leg and a corresponding inflatable chamber, said exhaust valve further facilitating graduated static pressure in said inflatable chambers.

14. An apparatus as recited in claim 13, wherein said exhaust valve comprises a spring loaded ball against an inlet orifice.

15. An apparatus as recited in claim 13, wherein said exhaust valve comprises a spring loaded disk against an inlet orifice.

16. An apparatus as recited in claim 10, wherein said means for introducing a fluid comprises a connective member.

17. An apparatus as recited in claim 16, wherein said connective member is removably attached to each inflatable chamber.

18. An apparatus as recited in claim 10, further comprising a foot inflatable chamber.

19. An apparatus for providing prophylaxis against deep vein thrombosis, comprising:

(a) at least two inflatable chambers adapted for placement on a leg of a patient such that said inflatable chambers are separated from each other to allow observation of the leg exposed therebetween, said inflatable chambers including an ankle inflatable chamber, each of said inflatable chambers being adapted to apply a compressive force to the portion of the leg upon which each said inflatable chamber is placed;

(b) at least one connective member associated with each of said inflatable chambers for introduction of fluid into each of said inflatable chambers; and (c) at least one pressure regulator associated with each of said inflatable chambers designed to regulate pressure in a dynamic compression phase and a static compression phase within each of said inflatable chambers such that the dynamic compression phase and the static compression phase are independently controlled in each inflatable chamber, the dynamic compression phase establishing and maintaining a pressure in each of said inflatable chambers sufficient to effect movement of blood from the portion of the leg upon which each inflatable chamber is placed; and the static compression phase establishing a pressure gradient across said inflatable chambers wherein the highest pressure of said gradient is established in said ankle inflatable chamber, and the lowest pressure of said gradient is established within a more proximal inflatable chamber, the static compression phase effecting a minimum pressure on the leg of the patient throughout attachment of the apparatus to the leg;

wherein each of the inflatable chambers is maintained during the static compression phase at static pressures sufficiently reduced below the dynamic compression phase in order to effect movement of blood back into the portion of the leg from which blood was removed during the dynamic compression phase.

20. An apparatus as recited in claim 19, wherein said inflatable chambers further comprise retaining straps including hook and pile material for retention of said inflatable chambers substantially against selected portions of the leg.

21. An apparatus as recited in claim 19, further comprising a regulator valve including an exhaust valve directed to a predetermined pressure level for an area of the leg and a corresponding inflatable chamber, said exhaust valve further facilitating graduated static pressure in said inflatable chambers.

22. An apparatus as recited in claim 21, wherein said exhaust valve comprises a spring loaded ball against an inlet orifice.

23. An apparatus as recited in claim 21, wherein said exhaust valve comprises a spring loaded disk against an inlet orifice.

24. An apparatus as recited in claim 19, wherein said connective member is removably attached to each inflatable chamber.

25. An apparatus as recited in claim 19, further comprising a foot inflatable chamber.

26. A method for providing prophylaxis against deep vein thrombosis comprising the steps of:

(a) obtaining at least first and second inflatable chambers;

(b) positioning said first inflatable chamber at the ankle of a leg of a patient and said second inflatable chamber between the ankle and hip such that said first and second inflatable chambers are separated from each other to allow observation of the leg exposed therebetween;

(c) applying a dynamic pressure independently to said first and second inflatable chambers in order to disgorge blood from the leg of the patient;

(d) allowing the dynamic pressure to remain in said first and second inflatable chambers;

(e) removing pressure from said first and second inflatable chambers until a graduated static pressure is achieved such that said first inflatable chamber maintains a higher static pressure level than said second inflatable chamber, the static pressure effecting a minimum pressure on the leg of the patient throughout attachment of the apparatus to the leg; and (f) repeating steps (c) through (e), above, as long as desired to effectuate vascular assist.

27. A method as recited in claim 26, wherein said at least first and second inflatable chambers are pressurized to an equal pressure level.

28. A method as recited in claim 26, wherein said at least first and second inflatable chambers are inflated to a uniform dynamic pressure of about 50 mmHg to about 150 mmHg.

29. A method as recited in claim 26, wherein said first inflatable chamber is inflated for about three seconds to a pressure level from about 50 mmHg to 150 mmHg.

30. A method as recited in claim 29, wherein said second inflatable chamber is inflated for three seconds to a pressure level from about 50 mmHg to about 150 mmHg after a delay of about one half second to about four seconds from inflation of said first inflatable chamber.

31. A method as recited in claim 26, wherein said first inflatable chamber is deflated for about 17 seconds to about 60 seconds to a pressure level from about 15 mmHg to about 25 mmHg.

32. A method as recited in claim 26, wherein said second inflatable chamber is deflated for about 17 seconds to about 60 seconds to a pressure level from about 10 mmHg to about 20 mmHg.

33. A method as recited in claim 26, wherein said at least first and second inflatable chambers are inflated to different pressure levels.

34. A method as recited in claim 26, further comprising the step of positioning a foot inflatable chamber at the foot of said patient.

35. An apparatus for providing prophylaxis against deep vein thrombosis, comprising:

(a) a compressive sleeve including a foot inflatable chamber, an ankle inflatable chamber, a calf inflatable chamber, and a thigh inflatable chamber, each inflatable chamber being adapted to apply a compressive force to a portion of the leg upon which the inflatable chamber is placed, the inflatable chambers separated from each other to allow observation of the leg therebetween, at least one of the inflatable chambers having a plurality of subchambers with substantially the same volume; and (b) means for independently generating and regulating pressure in a dynamic compression phase and a static compression phase within each of the inflatable chambers, the dynamic compression phase effecting movement of blood from the leg and the static compression phase establishing a static pressure gradient across the inflatable chambers thereby effecting movement of blood back into the portion of the leg from which blood was removed during the dynamic compression phase, the static compression phase effecting a minimum pressure on the leg.

* * * * *